United States Patent
Felder

(10) Patent No.: US 9,216,386 B2
(45) Date of Patent: Dec. 22, 2015

(54) SEQUENTIAL EXTRACORPOREAL TREATMENT OF BODILY FLUIDS

(75) Inventor: Mitchell S. Felder, Hermitage, PA (US)

(73) Assignee: Marv Enterprises, LLC, Hermitage, PA (US)

(*) Notice: Subject to any disclaimer, the term of this patent is extended or adjusted under 35 U.S.C. 154(b) by 0 days.

(21) Appl. No.: 13/254,855

(22) PCT Filed: Mar. 16, 2010

(86) PCT No.: PCT/US2010/027474
§ 371 (c)(1),
(2), (4) Date: Sep. 5, 2011

(87) PCT Pub. No.: WO2010/107789
PCT Pub. Date: Sep. 23, 2010

(65) Prior Publication Data
US 2012/0000838 A1    Jan. 5, 2012

Related U.S. Application Data

(60) Provisional application No. 61/160,755, filed on Mar. 17, 2009, provisional application No. 61/218,446, filed on Jun. 19, 2009.

(51) Int. Cl.
*A61M 37/00* (2006.01)
*B01D 61/24* (2006.01)
(Continued)

(52) U.S. Cl.
CPC ............ *B01D 61/243* (2013.01); *A61M 1/362* (2014.02); *A61M 1/369* (2013.01); *A61M 1/3615* (2014.02); *A61M 1/3681* (2013.01); *A61M 1/3687* (2013.01); *B01D 61/28* (2013.01); *A61M 1/16* (2013.01); *A61M 2202/0405* (2013.01); *A61M 2202/0464* (2013.01); *Y10T 137/0318* (2015.04); *Y10T 137/794* (2015.04)

(58) Field of Classification Search
CPC ... A61M 1/369; A61M 1/3615; A61M 1/362; A61M 1/16; A61M 1/3689; A61M 1/3687; A61M 1/3679; A61M 1/3486; A61M 1/3493; A61M 1/3686; A61M 2202/0405; A61M 2202/0464; B01D 61/243; B01D 61/28; Y10T 137/794; A61K 2039/505
USPC ............ 604/5.01, 5.04, 6.01–6.06, 6.08–6.09
See application file for complete search history.

(56) References Cited

U.S. PATENT DOCUMENTS 4,048,064 A    9/1977    Clark
4,381,004 A *  4/1983    Babb ............................ 604/5.02
(Continued)

FOREIGN PATENT DOCUMENTS

WO    WO 2013/028451 A1    2/2013

*Primary Examiner* — Philip R Wiest
*Assistant Examiner* — Ariana Zimbouski

(57) ABSTRACT

An article and method to treat extracorporeally a patient's bodily fluid. The bodily fluid can include blood, cerebral spinal fluid and lymph. A first stage of the method includes applying a treatment. The treatment can comprise dosing with a medication, thermal treatment, or irradiation. The treatment can occur at levels that could otherwise compromise the patient's health. A second stage of the method substantially removes the treatment from the bodily fluid. The bodily fluid can then be returned to the patient. The article includes a treatment chamber that applies the treatment and a removal module for removing the treatment. The method can be a continuous process such as, for example, a dialysis process.

9 Claims, 1 Drawing Sheet

(51) Int. Cl.
*A61M 1/36* (2006.01)
*B01D 61/28* (2006.01)
*A61M 1/16* (2006.01)

(56) References Cited

U.S. PATENT DOCUMENTS

| | | | |
|---|---|---|---|
| 4,950,225 | A | 8/1990 | Davidner |
| 5,047,321 | A | 9/1991 | Loken |
| 5,069,662 | A | 12/1991 | Bodden |
| 5,277,820 | A | 1/1994 | Ash |
| 5,466,574 | A | 11/1995 | Liberti et al. |
| 5,514,340 | A | 5/1996 | Lansdorp et al. |
| 5,853,722 | A | 12/1998 | Rollins |
| 6,171,777 | B1 | 1/2001 | Cook et al. |
| 6,676,622 | B2 * | 1/2004 | Strahilevitz .............. 604/5.01 |
| 6,821,790 | B2 * | 11/2004 | Mahant et al. ............. 436/177 |
| 7,018,395 | B2 * | 3/2006 | Chen .............................. 607/88 |
| 8,057,418 | B2 * | 11/2011 | Korbling et al. ........... 604/5.02 |
| 2004/0189311 | A1 | 9/2004 | Glezer |
| 2004/0215173 | A1 | 10/2004 | Kunst |
| 2005/0242033 | A1 | 11/2005 | Tu |
| 2005/0271653 | A1 | 12/2005 | Strahilevitz |
| 2006/0025713 | A1 | 2/2006 | Rosengart et al. |
| 2008/0145333 | A1 * | 6/2008 | Lentz ........................... 424/85.2 |
| 2008/0195024 | A1 | 8/2008 | Schmid-Schonbein |
| 2009/0068194 | A1 * | 3/2009 | Julien et al. ............... 424/146.1 |
| 2009/0191217 | A1 * | 7/2009 | de Wildt et al. ........... 424/158.1 |
| 2010/0030196 | A1 | 2/2010 | Hildebrand |
| 2011/0009312 | A1 * | 1/2011 | Rosen et al. .................. 514/1.9 |
| 2011/0098623 | A1 | 4/2011 | Zhang |
| 2011/0160636 | A1 * | 6/2011 | Bansal ......................... 604/6.09 |
| 2011/0295175 | A1 * | 12/2011 | Felder et al. ................ 604/5.01 |

\* cited by examiner

SEQUENTIAL EXTRACORPOREAL TREATMENT OF BODILY FLUIDS

FIELD OF THE INVENTION

The invention relates to an article and method of sequentially and extra-corporeally applying a treatment to a patient's bodily fluid and then removing the treatment from the bodily fluid before returning the bodily fluid to the patient.

BACKGROUND OF THE INVENTION

Dialysis machines are well known in the art. Blood is removed from a patient's bloodstream, passes through the dialysis machine, and returns to the patient. The dialysis machine can remove contaminants from the blood.

Prior art includes in vivo treatment of a patient with a toxic medication that can be non-metabolizable. The medication pervades the bloodstream and organs of the patient. The toxic medication affects both healthy and diseased organs.

SUMMARY OF THE INVENTION

The present invention relates to an article and method of excorporeally treating a patient's bodily fluid. Treatment can include, for example, delivery of a medication, thermal treatment, irradiation, and combinations thereof. After treatment, the treatment can be removed, such as, by dialysis of the medication, and the bodily fluid can be returned to the patient. The bodily fluid can include blood, cerebral spinal fluid, and lymph.

The article and method permit treatments that could otherwise be dangerous if given in vivo. Medication can be administered in doses that are many times higher than would normally be considered safe. Thermal treatment can heat or chill the extracorporeal bodily fluid beyond the ability of a patient to otherwise endure. Irradiation can specifically target bodily fluid-borne pathogens or carcinoma cells without compromising vital organs or systems.

The method includes providing a dialysis machine including a first stage and a second stage, and sequentially passing extracorporeal bodily fluid through the first and second stages. The bodily fluid is removed from the patient, such as from the patient's bloodstream. The first stage applies a treatment to the bodily fluid. The second stage substantially removes the treatment. The bodily fluid is then returned to the patient.

In embodiments, the treatment includes releasing a medication into the treatment chamber until an effective medication concentration is achieved in the bodily fluid. Returning the bodily fluid substantially to the initial condition includes lowering the medication concentration in the bodily fluid to a safe level. In alternative embodiments, the first stage can irradiate the bodily fluid so as to interrupt mitosis of pathogens or carcinoma cells. Radiation can include, for example, ultraviolet, x-ray, microwave radiation, radio waves, and combinations thereof.

The article includes a two-stage device. A first stage includes a treatment chamber for applying a treatment to the extracorporeal bodily fluid. A second stage receives the treated extracorporeal bodily fluid and includes a unit for removing the treatment. In embodiments, the first stage comprises a dialysis tube having an exterior wall defining a treatment chamber. An interior wall can define a delivery tube within the chamber. The delivery tube can deliver the treatment such as, for example, a medication or irradiation. The delivery tube can also heat or chill the bodily fluid. In embodiments, the delivery tube can include a helical coil. The second stage can include, for example, a dialysis unit, a filter for removal of mechanical or chemical moieties, or heater or chiller.

DETAILED DESCRIPTION OF THE INVENTION

The method of the invention includes removing bodily fluid from a patient, applying in a first stage a treatment to the extracorporeal bodily fluid, removing the treatment in a second stage, and returning the extracorporeal bodily fluid to the patient. Conveniently, the extracorporeal bodily fluid enters a device comprising the first stage and the second stage. The first stage includes a treatment chamber for applying the treatment. The second stage removes the treatment from the bodily fluid. Bodily fluid includes blood, cerebral spinal fluid, and lymph. It is to be understood that reference to one bodily fluid can incorporate the others.

The treatment can include any treatment known to one skilled in the art including, for example, dosing with a medication, heating the bodily fluid, cooling the bodily fluid, irradiating the bodily fluid, targeting a pathogen or chemical moiety, and combinations thereof. Pathogens can include, for example, a bacterium, virus, fungus, prion, targeted antigen, and combinations thereof. Chemicals can include, for example, proteins such as albumin, antibodies, and lipids such as cholesterol. The appropriate treatment will depend on the patient's condition. Treatment can be effective against various blood-borne pathogens including, but not limited to, viruses, bacteria, fungi, cancers, prions or targeted antigens. For example, medical imaging can identify the blood supply of a tumor. The arterial and/or venous blood from the tumor can be removed, treated, and replaced so as to reduce the likelihood of metastasis.

Factors affecting the treatment can include for example the contact surface area with the bodily fluid, the composition of the first stage, charge interactions, binding interactions, and combinations thereof. The second stage substantially removes the treatment from the extracorporeal bodily fluid. Depending on the treatment, the second stage can include, for example, a mechanical filter, a chemical filter, a molecular filter, a chiller, a heater, or combinations thereof.

Advantageously, the method permits treatments that would be hazardous or even lethal if administered in vivo. For example, the treatment can include adding a medication to the extracorporeal bodily fluid at concentrations that a patient could not tolerate if administered in vivo. Similarly, the extracorporeal bodily fluid can be heated or chilled to temperatures that would otherwise be injurious to a patient's health. Radiation levels can be substantially greater and the proximity of the radiation source to the pathogen or carcinoma cells can be significantly closer.

During the process, the patient can be given at least one transfusion. The transfusion can maintain blood volume while a portion of the patient's blood is undergoing the process, that is, outside of the patient's body.

Figure 1:
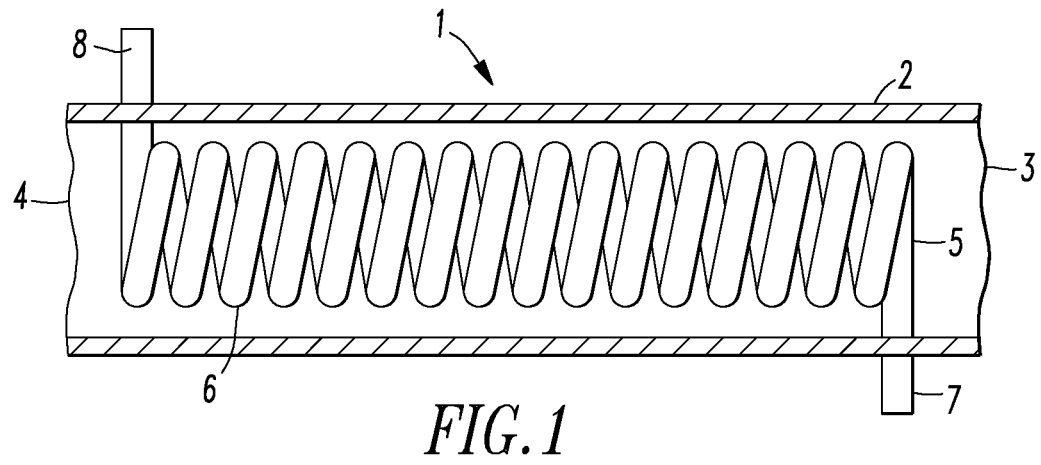
FIG. 1 shows a cross-section of an embodiment of a first stage.

The device of the invention includes a first stage and a second stage. The first stage applies a treatment to extracorporeal bodily fluid. The second stage includes a removal module that substantially removes the treatment from the extracorporeal bodily fluid. As shown in FIG. 1, the first stage 1 can include an exterior wall 2 defining a treatment chamber 5. The treatment conveniently can be applied in the treatment chamber 5. The dimensions of the treatment chamber 5 can vary depending on the treatment to be applied. For example, certain forms of radiation have limited depths of penetration, so the treatment chamber 5 can be correspondingly narrow. Alternatively, residence times of the bodily fluid can be altered by changing the dimensions of the treatment chamber or by using a dialysis vacuum pump.

With reference to FIG. 1, bodily fluid enters the inlet 3, passes through the treatment chamber 5, and exits the outlet 4. In embodiments, the treatment can be applied from a delivery tube 6 located within the treatment chamber 5. An interior wall 9 defines the delivery tube 6. The delivery tube 6 can include at least one lead 7, 8. The lead 7, 8 can deliver the treatment to the treatment chamber 5. Conveniently, the delivery tube 6 will have a high contact surface area with the bodily fluid. As shown, the delivery tube 6 comprises a helical coil.

Figure 2:
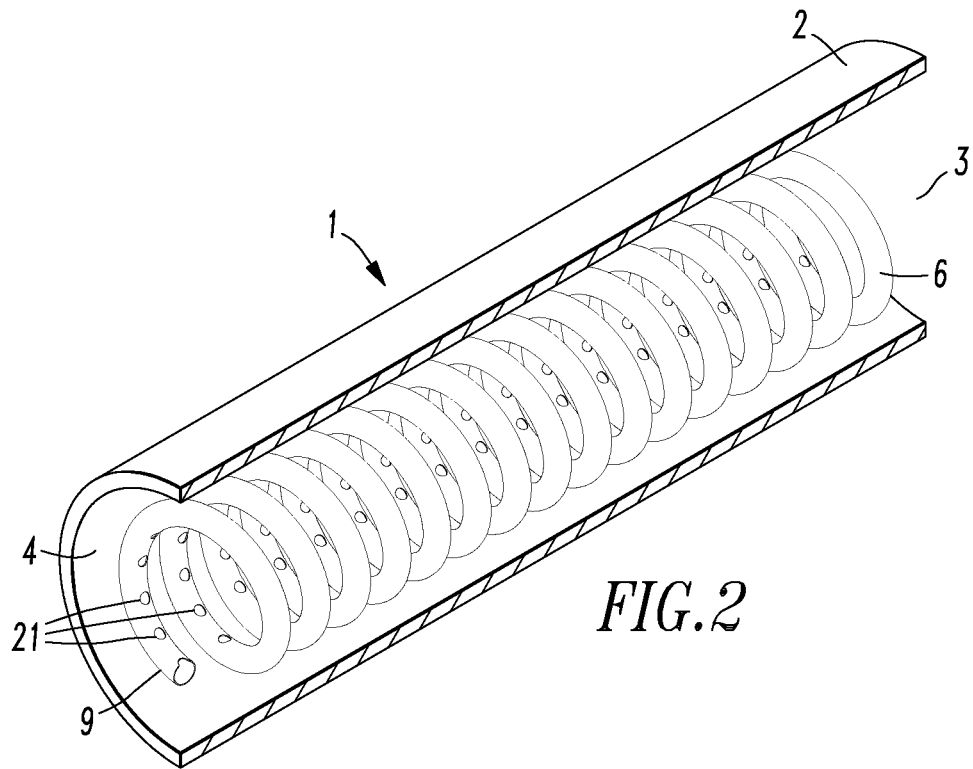
FIG. 2 shows an alternative embodiment of the first stage.

With reference to FIG. 2, when the treatment includes the administration of a medication, the delivery tube 6 can be hollow and the interior wall 9 can define a plurality of holes 21. The medication can be pumped through the delivery tube 6 in order to effect a desired concentration of medication in the bodily fluid. The medication can perfuse through the holes 21. The delivery tube 6 can include any suitable material including, for example, metal, plastic, ceramic or combinations thereof. The delivery tube 6 can also be rigid or flexible. In one embodiment, the delivery tube 6 is a metal tube perforated with a plurality of holes. Alternatively, the delivery tube 6 can be a plastic. The plastic can include a fabric.

The medication can be delivered in a concurrent or countercurrent mode with reference to the bodily fluid. In countercurrent mode, the bodily fluid enters the treatment chamber 5 at the inlet 3. Medication can enter through a first lead 8 near the outlet 4 of the treatment chamber 5. Bodily fluid passes to the outlet 4 and medication passes to the second lead 7 near the inlet 3.

In alternative treatments, the delivery tube can comprise a radiation-emitting bulb, such as a UV bulb or other radiation emitter. The delivery tube can also include a heating element or cooling element for thermal treatment of the bodily fluid.

The removal module of the second stage can substantially remove the treatment from the extracorporeal bodily fluid. Of course, when appropriate, the second stage can leave a portion of treatment in the bodily fluid that is returned to the patient. For example, the second stage can permit a therapeutic quantity of chemotherapeutic agent to remain in the bodily fluid in order to treat an underlying metastasis. This technique permits high dose, extracorporeal treatment and intercorporeal treatment at standard chemotherapeutic dose concentrations.

The second stage can include a filter, such as a dialysis machine, which is known to one skilled in the art. U.S. Pat. No. 6,036,858 to Carlsson et al. and U.S. Pat. No. 3,598,727 to Willock are hereby incorporated by reference. The second stage can also adjust the temperature of the bodily fluid. The second stage can include a molecular filter. For example, a molecular adsorbants recirculating system (MARS), which may be compatible with dialysis equipment. MARS technology can be used to remove small to average sized molecules from the bodily fluid. Artificial liver filtration presently uses this technique.

The invention can include a plurality of steps for removing a targeted moiety, such as, for example a cancer cell, pathogen, or chemical. A first step can include directing a first antibody against the targeted moiety. A second step can include a second antibody. The second antibody can be conjugated with albumin. The second antibody or antibody-albumin complex combines with the first antibody forming an antibody-antibody-moiety complex. A third step can remove the complex from the bodily fluid, such as with dialysis/MARS. The purified bodily fluid can be returned to the patient.

In practice, a portion of the purified bodily fluid can be tested to ensure a sufficient portion of the complex has been removed from the extracorporeal bodily fluid. Testing can determine the length of treatment and evaluate the efficacy of the sequential dialysis method in removing targeted moieties. Bodily fluid with an unacceptably large concentration of complex remaining can be re-filtered before returning to the patient.

The invention can be used in combination with an albumin-bound antibody. The albumin-bound antibody can complex with a pathogen or chemical, and so improve removal of the pathogen or chemical from the bodily fluid. For example, an antibody-albumin complex can be combined with Methicillin-resistant *Staphylococcus aureus* (MRSA) in the bodily fluid. The dialysis/MARS methodology can be configured to remove the antibody-albumin-MRSA complex from the bodily fluid. This technique can be used in the removal of other pathogens including, for example, HIV and leukemia cells.

In embodiments, the second stage can remove a medication by various techniques including, for example, filtering based on molecular size, protein binding, solubility, chemical reactivity, and combinations thereof. For example, a filter can include a molecular sieve, such as a zeolite, or porous membranes that captures medications comprising molecules above a certain size. Membranes can comprise polyacrylonitrile, polysulfone, polyamides, cellulose, cellulose acetates, polyacrylates, polymethylmethacrylates, and combinations thereof. Additionally, the membrane can be charged to capture charged medications. Increasing the flow rate or dialysate flow rate can increase the rate of removal of the medication.

Techniques can include continuous renal replacement therapy (CRRT) which can remove large quantities of filterable medication in the plasma. CRRT is particularly useful for medications that are not strongly bound to plasma proteins. Categories of CRRT include continuous arteriovenous hemofiltration, continuous venovenous hemofiltration, continuous arteriovenous hemodiafiltration, slow continuous filtration, continuous arteriovenous high-flux hemodialysis, and continuous venovenous high flux hemodialysis.

The sieving coefficient (SC) is the ratio of the medication concentration in the filtrate to the incoming plasma. A SC close to zero implies that the medication will not pass through the filter. One skilled in the art will appreciate that the particular CRRT technique will depend on specific conditions. A filtration rate of 50 ml/min is generally satisfactory. Preferably, the medication will be non-protein binding. Other methods of increasing removability of medication include the use of acidic medications, acidification of the medication, the use of organic acids to compete with protein binding sites.

Molecules that are lipophilic or highly protein bound can be removed using plasmapheresis. In such cases, transfusions or plasma may be given to the patient to compensate for any discarded plasma.

The invention can also be used in combination with other therapies including, for example, Kanzius radiofrequency (RF) therapy as described in U.S. Pat. No. 7,510,555 and U.S. Pat. No. 7,627,381 which are hereby incorporated by reference. Kanzius therapy uses nanoparticles and RF radiation to induce hyperthermia in cancer cells.

The invention and Kanzius therapy are synergistic. Alone, Kanzius therapy can cause multiple infarctions in major organs leading to blindness, heart attacks, and renal failure. Performing Kanzius therapy extracorporeally avoids these morbidities. Additionally, much higher levels of RF can be used. The invention can include removing the patient's venous blood leaving a tumor, treating the extracorporeal blood in a first stage comprising Kanzius therapy, removing from the blood in a second stage the nanoparticle residue of the Kanzius therapy and cellular and/or pathogen debris, and returning the blood to the patient. Reducing the residue and debris returned to the patient's vascular system can reduce deleterious vascular cascades such as coagulation and inflammation, which are further causes of patient morbidity.

Advantageously, a physician can use magnetic resonance angiography (MRA) or magnetic resonance venography (MRV) to determine the arterial and venous blood vessels to and from a tumor.

EXAMPLE 1

Blood is removed from a patient and passed through a treatment chamber in which a first stage of treatment is applied. The first stage includes inducing an antibody/antigen reaction using a specially designed antibody. A second stage efficaciously removes the product using a combination dialysis and MARS device. The antibody is conjugated with an albumin compound; however, any convenient compound that can conjugate with the antibody and can be removed using dialysis and MARS is suitable. The antibody-albumin complex binds to targeted antigens such as targeted antigens on carcinoma cells and/or proteins associated with carcinomas, such as proteins affecting angiogenesis and/or increased metastatic rates in carcinomas. These proteins can include vascular endothelial growth factor (VEGF), receptor tyrosine kinases such as Tie-1 and Tie-2, basic fibroblast growth factor (bFGF), Large T (a SV40 virus protein), Muc4 (a mucin protein associated the spread of breast cancer), and angioproteins such as, for example, Ang1, Ang2, Ang3 and Ang4. After application of the treatment in the first stage, the blood moves to a second stage in which the treatment is removed. The second stage includes a MARS device for the removal of the carcinoma proteins. The albumin-bound antibody facilitates removal of the protein using the MARS device.

EXAMPLE 2

Blood is removed from a patient and passed through a treatment chamber in which a first stage of treatment is applied. The first stage includes targeting a pathogen in the blood. The pathogen can include at least one bacterium, virus, fungus or prion. After the blood leaves the treatment chamber, the second stage removes the pathogen using a mechanical filter or a MARS device.

EXAMPLE 3

In a first stage of the present invention, the MRSA bacteria can be complexed with a binding protein or antigen. A protein can include, for example, PBP2a that binds to the penicillin-binding protein 2a antigen. An antigen can include, for example, a *staphylococcus aureus* cell membrane antigen. In a second stage, the complex can be removed from the patient's blood using the present invention thereby reducing the population of MRSA bacteria. The complex can occur either in vivo or in a first stage of the method.

EXAMPLE 4

Similar to the methods of examples 1, 2 and 3, the invention can be used to treat HIV. Suitable antibodies can include targeted antigens for HIV p17 antigen peptide HGP-30, env protein gp 36 HIV, p15 gag protein HIV, gag protein p 26 HIV, gp 110 env protein HIV, TAB9, HIV-1 protein p 31 HIV1, HIV-1 gp 160, and transmembrane protein HIV-2. Antibodies can be added in a first stage to form an antibody-virus complex. The complex can be removed in a second stage.

EXAMPLE 5

The method can be used to treat tauopathies, which are pathological aggregation of tau protein in neurofibrillary tangles in the human brain. Taupathies include Alzheimer's Disease, Pick's Disease (Frontotemporal Lobar degeneration), Progressive Supranuclear Palsy, Corticobasal degeneration, Frontotemporal dementia, Dementia pugilistica, and Creutzfeldt-Jakob disease. Tau inclusions, that is, hyperphosphorylation of the tau protein, induces the formation of filaments and neurofibrillary tangles of paired helical filaments. The method includes a first stage that combines the tau protein in the cerebral spinal fluid with an antibody-albumin complex. The treated cerebral spinal fluid can pass through a second stage where the antibody-albumin-protein complex can be removed before returning the blood to the patient. The second stage can include a mechanical filter or a MARS device.

EXAMPLE 6

The invention can be used to disrupt the pathophysiologic etiologies of amyotrophic lateral sclerosis (ALS). Etiologies of ALS include (i) the excitotoxicity of anterior motor neurons due to a defective uptake of glutamate into astrocytes, (ii) an abnormal superoxide dismutase proteins, or (iii) an aggregation of SOD1 protein. The method includes removing cerebrospinal fluid (CSF) from a patient and passing the CSF into a first stage. The first stage applies a treatment that targets at least one etiology. The treatment includes targeting an etiology with at least one complexing agent such as, for example, an antibody-albumin complex. The complexing agent combines with the etiology to produce a combination that can be removed from the CSF in a second stage. The second stage can comprise sequential dialysis/MARS. The CSF can then be returned to the patient.

EXAMPLE 7

The method can be used to remove cholesterol and other lipids from the bloodstream. Blood is removed from the patient and treated in a first stage with an anticholesterol-antibody complex that binds to the lipid. The complex can include IgM and IgG isotypes. The treated blood is passed through a second stage comprising a dialysis/MARS device.

EXAMPLE 8

Blood is removed from a patient's bloodstream. The blood passes through a first stage where Kanzius therapy is applied. The therapy includes targeting a moiety such as a cancer cell, bacteria, virus, fungus, prion. The therapy uses nanoparticles and radiation to induce apaptosis in targeted moieties. The Kanzius therapy can include lead nanoparticles bound to antibodies. A second stage can remove from the blood the residue and debris created by Kanzius therapy. The blood is then returned to the patient. The second stage removal process can include, for example, a strong magnetic field.

What is believed to be the best mode of the invention has been described above. However, it will be apparent to those skilled in the art that numerous variations of the type described could be made to the present invention without departing from the spirit of the invention. The scope of the present invention is defined by the broad general meaning of the terms in which the claims are expressed.

The invention claimed is:

1. A method for treating an extracorporeal bodily fluid comprising:
   a. Applying a treatment to a moiety in the extracorporeal bodily fluid in a first stage comprising forming an antibody-antibody-moiety complex by targeting a first antibody to the moiety and conjugating with a second antibody including albumin;
   b. Passing the extracorporeal bodily fluid to a second stage; and
   c. Removing at least a portion of the antibody-antibody-moiety complex from the extracorporeal bodily fluid in the second stage.

2. The method of claim 1, wherein removing the antibody-antibody-moiety complex is achieved by a process selected from the group consisting of dosing with a medication, heating the extracorporeal bodily fluid, cooling the extracorporeal bodily fluid, targeting a moiety, and combinations thereof.

3. The method of claim 2, wherein the moiety is selected from the group consisting of a pathogen, a chemical, and combinations thereof.

4. The method of claim 3, wherein the pathogen is selected from the group consisting of a bacterium, virus, fungus, prion, and combinations thereof.

5. The method of claim 3, wherein the chemical is selected from the group consisting of a protein, lipid, antibody, antigen, and combinations thereof.

6. The method of claim 1, wherein the extracorporeal bodily fluid is selected from the group consisting of blood, cerebral spinal fluid, and lymph.

7. The method of claim 1, wherein the moiety is selected from the group consisting of vascular endothelial growth factor (VEGF), receptor tyrosine kinases, basic fibroblast growth factor (bFGF), large T (a SV40 virus protein), Muc4 (a mucin protein associated with the spread of breast cancer), and angioproteins.

8. The method of claim 1, wherein the moiety is selected from the group consisting of HIV p17 antigen peptide HGP-30, env protein gp 36 HIV, p15 gag protein HIV, gag protein p 26 HIV, gp 110 env protein HIV, TAB9, HIV-1 protein p 31 HIV1, HIV-1 gp 160, and transmembrane protein HIV-2.

9. The method of claim 1, wherein the moiety is selected from the group consisting of an abnormal superoxide dismutase protein, an aggregation of SOD1 protein, and combinations thereof.

* * * * *